US00PP14976P2

(12) United States Plant Patent
Dufresne

(10) Patent No.: US PP14,976 P2
(45) Date of Patent: Jul. 6, 2004

(54) SALVIA PLANT NAMED 'RFD-S016'

(50) Latin Name: *S. greggii*
Varietal Denomination: RFD-S016

(76) Inventor: Richard Frederick Dufresne, 313 Spur Rd., Greensboro, NC (US) 27406

( * ) Notice: Subject to any disclaimer, the term of this patent is extended or adjusted under 35 U.S.C. 154(b) by 110 days.

(21) Appl. No.: 10/186,079

(22) Filed: Jun. 28, 2002

(51) Int. Cl.[7] ..... A01H 5/00
(52) U.S. Cl. ..... Plt./226
(58) Field of Search ..... Plt./226, 263

*Primary Examiner*—Bruce R. Campell
*Assistant Examiner*—June Hwu

(57) ABSTRACT

A new cultivar of Salvia plant named 'RFD-S016' that is distinguished by its rich, clear orange-red color. This trait sets 'RFD-S016' apart from all other existing varieties of Salvia known to the inventor.

2 Drawing Sheets

Genus: Salvia.
Species: *greggii.*
Denomination: 'RFD-S016'.

BACKGROUND OF THE INVENTION

The present invention relates to a new variety of *S. greggii* Gray, hereinafter referred to by the cultivar name 'RFD-S016'. 'RFD-S016' originated as a chance seedling from a potted plant found in the inventor's collection as above at Greensboro, N.C., in August 1995. 'RFD-S016' was taken from the pot of a *S. greggii* Gray variety and maintained for asexual propagation purposes. The inventor presumes that 'RFD-S016' is a seedling of the adjacent plant, *S. greggii* Gray.

The inventor has been studying, collecting, and disseminating Salvia species for twenty-seven years. During this period, he has traded Salvia species and cultivars with many botanical gardens and nurseries.

One of the inventor's goals has been to sort out confusion on the identities of various forms of Salvias being marketed. This has necessitated developing contacts with various herbaria and taxonomic experts to assist with the proper identification of Salvia forms. The developed information has been supplied at times to Salvia collectors and to nurseries and botanic gardens where visits have been made to check on the correct identification of various Salvias. Collected results of the identification of Salvias, along with horticultural information like zone hardiness, size, and bloom period and flower color have been reported in his publication, the Salvia Placard Handbook. Recently, the World of Salvia web site was created and is being maintained for the purpose of reporting this information about Salvias to the public.

The inventor has bred and introduced many successful commercial introductions, including *Salvia greggii* Gray hybrids 'Cherry Chief' (unpatented), 'Cherry Queen' (unpatented), 'Maraschino' (unpatented), and 'Raspberry Royale' (unpatented).

'RFD-S016' is distinguished from other varieties of the species known to the inventor, and was selected for this distinguishing feature, namely that the flowers of RFD-S016 are rich, clear orange-red in color.

'RFD-S016' was first asexually propagated in 1995 at Greensboro, N.C., USA using vegetative cuttings. It has been found to remain fixed, stable and uniform through several generations.

SUMMARY OF THE INVENTION

The following traits have been repeatedly observed and represent the distinguishing characteristics of 'RFD-S016'. In combination these traits set the new cultivar apart from all others existing varieties of Salvia known to the inventor. 'RFD-S016' has not been tested under all possible conditions and phenotypic differences may be observed with variations in environment, climatic, and cultural conditions, however, without any variance in genotype.

1. Salvia 'RFD-S016' exhibits a rich, clear orange-red color.

BRIEF DESCRIPTION OF THE DRAWINGS

The accompanying drawings illustrate the distinguishing traits of the new Salvia cultivar 'RFD-S016'. The photograph was taken in summer 2002 of a one year-old plant, in a 5-gallon container that was grown in a greenhouse in a cultivated area of Arroyo Grande, Calif., USA.

The drawing on sheet 1 illustrates the entire plant.

Sheet 2 is a close-up view of the flower. The drawings were made using conventional photographic techniques. Although colors may appear different from actual colors due to light reflectance, they are as accurate as possible by conventional photography.

BOTANICAL DESCRIPTION OF THE PLANT

The following is a detailed description of the Salvia plant named 'RFD-S016'. Data was collected in April 2001 from one year-old plants grown in one gallon containers in full sun at Greensboro, N.C., USA. Phenotypic differences may be observed with variation in environmental, climatic, and cultural conditions. The color determinations are in accordance with the 1986 Edition of The Royal Horticulture Society Colour Chart except where general color terms of ordinary dictionary significance are used. The growing requirements are similar to other Salvia plants.

Botanical classification: Salvia 'RFD-S016'.
Species: *greggii.*
Common name: Salvia.

Use: Ornamental Shrub.
Form: Bush.
Height: 0.8–1.2 meter.
Width: 0.7–0.9 meter.
Growth habit: Perennial.
Blooming season: From one month after breaking spring dormancy to first frost.
Lastingness of the blooms: 3 to 4 days.
Disease and pest susceptibility: Drought tolerant. Deer and rabbit resistant. Susceptible to sucking insects when stressed. Generally outgrows most bacterial and viral infections.
Stem:
*Color.*—From 144B (new growth) to 166A (mature).
*Shape.*—Rounded square.
*Diameter.*—0.7 mm–1.5 mm.
*Texture.*—Smooth to minutely farinaceous.
Leaf:
*Arrangement.*—Opposite.
*Shape.*—Elliptic to oblong.
*Length.*—2.0–3.0 centimeters.
*Width.*—1.0–1.7 centimeters.
*Margin.*—Shallowly crenulate towards midsection, entire towards base and apex.
*Thickness.*—Slightly fleshy.
*Venation.*—Veins barely visible.
*Color: (upper surface and lower surface).*—Varies between 137A and 137C.
*Apex.*—Shape: Obtusely rounded. Color: RHS 137A to 137C.
*Base.*—Shape: Acute to acuminate, sometimes oblique. Color range: RHS 137A–C.
*Petiole.*—Shape: Mostly carinate; alate towards leaf base. Length: 7–12 millimeters. Width: 0.5–1.4 millimeter. Color: RHS 143C.
Peduncle:
*Length.*—4.5 mm.
*Width.*—0.7 mm.
*Color.*—Ranges between 147A and 147B.
*Texture.*—Glandular, puberulent.
Flower:
*Inflorescence.*—Type: Terminal raceme. Length: 19 centimeters. Diameter: 3.8 cm–4.4 cm.
*Number.*—From 13 to 17 decussate pairs.
*Shape.*—Tubular, two-lipped.
Bud:
*Length* (*including calyx*).—14 mm.
*Length* (*immature flower*).—1.5 mm.
*Width* (*immature flower*).—3.5 mm.
*Color* (*immature flower*).—44A.
*Shape* (*immature flower*).—hemisphere.
*Surface texture* (*immature flower*).—Prominently hairy.
Pedicel:
*Length.*—4.5 millimeters.
*Width.*—0.7 millimeters.
*Pubescene.*—Glandular, puberulent.
*Color.*—RHS 147AB.
Calyx:
*Shape.*—Tapered cylinder, flared toward the apex.
*Rib number.*—10, longitudinal.
*Length.*—From 8 mm to 14 mm.
*Width.*—From 3.5 mm to 5.5 mm.
*Pubescence.*—Glandular, puberulent.
*Color.*—45C.
*Lobe.*—Upper: Number: 1. Shape: Acute. Length: 3.2 millimeters. Width: 2.4 millimeters. Lower: Number: 2. Shape: Acute. Length: 2.4 millimeters. Width: 2.7 millimeters. Corolla: Shape: Tubular proximally to two-lipped distally. Length: 2.67 centimeters. Diameter (maximum width of lower lip): 16.3 mm. Color: RHS 44A. Tube: Length: 16 millimeters. Width (measured directly under magnifying lens): 3.0 millimeters. Depth: 7.0 millimeters. Lip: Upper: Number: 1. Shape: Hood-like. Length: 9.5 millimeters. Lower: Number: 2 suborbicular. Shape: Banner-like, extended downward. Outline: Obovate. Length: 13.4 millimeters. Diameter at widest point: 16.3 millimeters. Depth: 8.8 millimeters.
Reproductive organs:
*Pistil.*—Stigma color: 36D.
*Style.*—Length: 2.6 centimeters. Color: 44D. Pubescence: Present toward tip. Attachment site: To a four-lobed ovary between the lobes. Ovary color: 145B.
*Stamen.*—Number: 2. Shape: Seesaw-like. Connective length: 12.8 millimeters. Filament length: 3.6 millimeters. Anther: Color: 158D. Attachment site: Outer end of the connective. Pollen: Color: 13A. Staminodes: Present. Invagination: Absent. Fertility: 2–4 glossy brown-black oblong-elliptic nutlets. Nutlets: Length: 4 mm. Width: 2 mm. Color: 200A. Shape: Oblong-elliptic.

I claim:

1. A new and distinct cultivar of Salvia plant named 'RFD-S016' as described and illustrated.

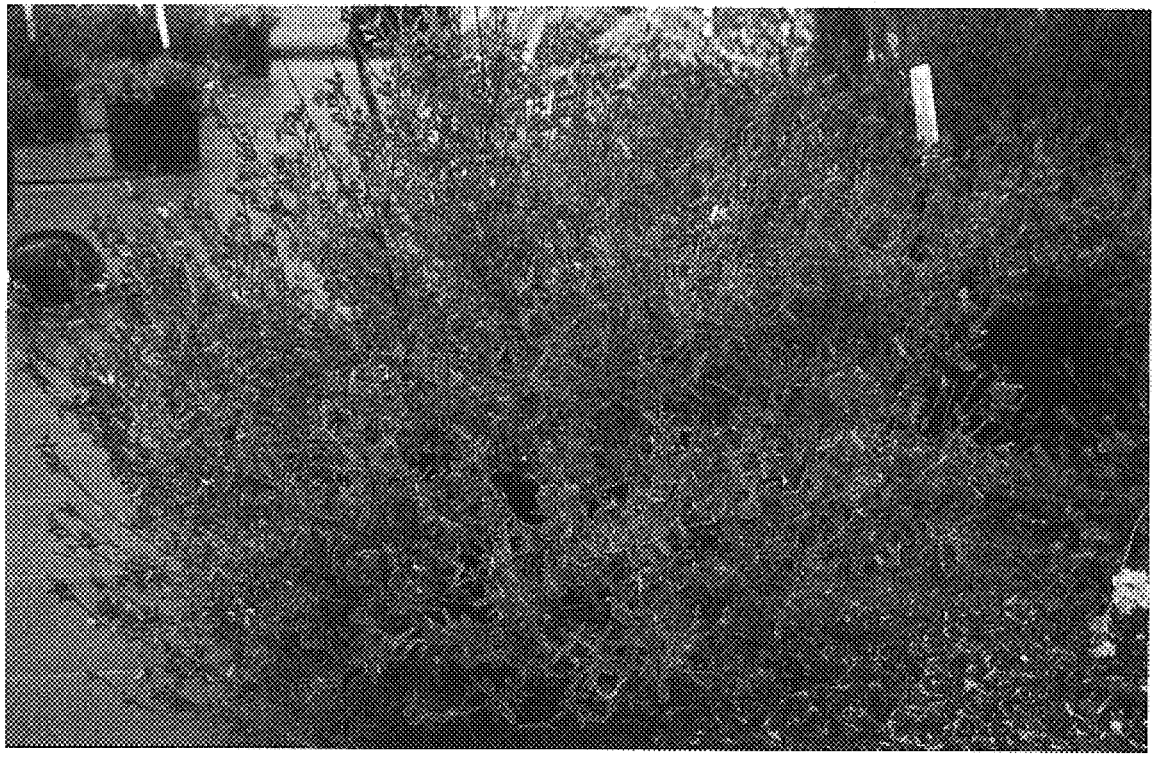

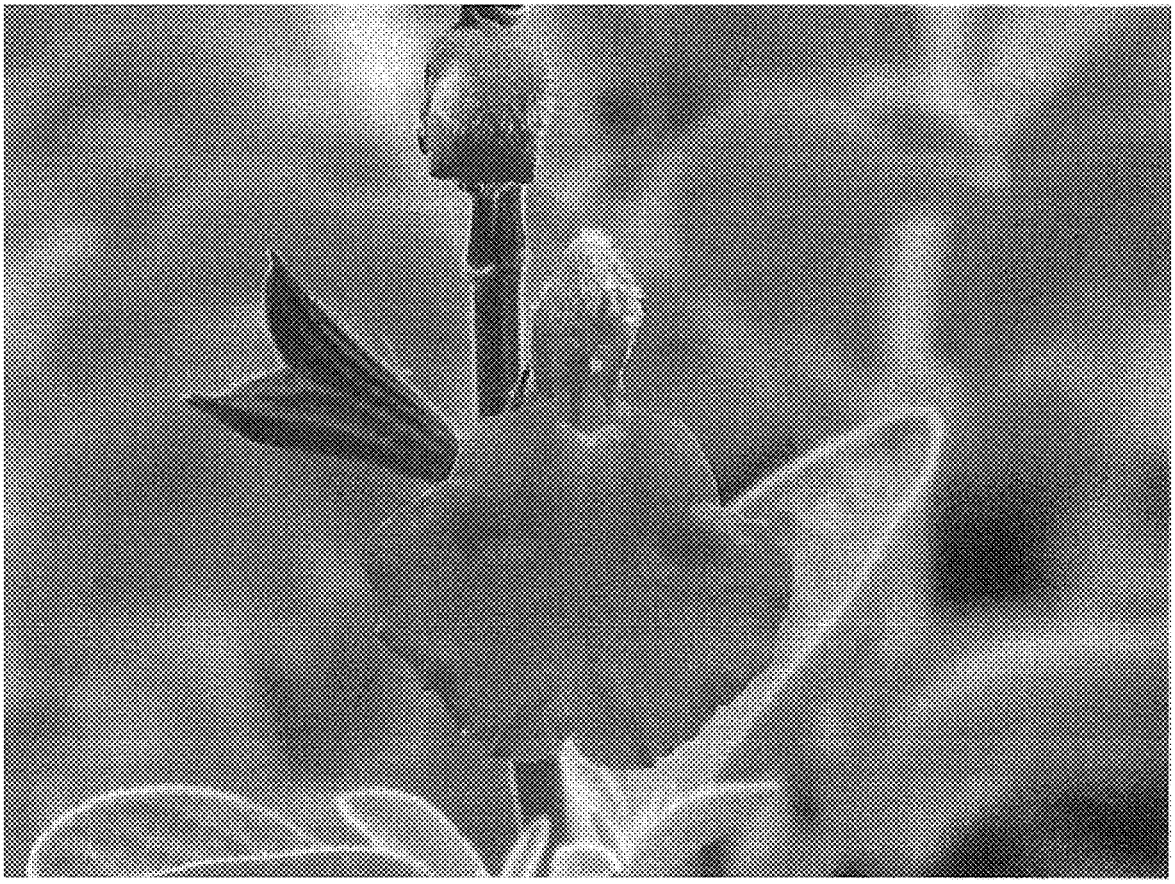

* * * * *